US008481008B2

(12) United States Patent
Decola et al.

(10) Patent No.: US 8,481,008 B2
(45) Date of Patent: *Jul. 9, 2013

(54) PHOTOTHERAPY COMPOSITIONS AND METHODS

(75) Inventors: Dennis Decola, Chadds Ford, PA (US); Curtis Cole, Ringoes, NJ (US)

(73) Assignee: Therakos, Inc., West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,103

(22) Filed: Sep. 23, 2011

(65) Prior Publication Data

US 2012/0039825 A1 Feb. 16, 2012

Related U.S. Application Data

(62) Division of application No. 11/311,714, filed on Dec. 19, 2005, now Pat. No. 8,057,785.

(60) Provisional application No. 60/638,213, filed on Dec. 22, 2004.

(51) Int. Cl.
| | |
|---|---|
| *A61K 8/00* | (2006.01) |
| *A61K 8/18* | (2006.01) |
| *A61K 9/00* | (2006.01) |
| *A61K 8/02* | (2006.01) |
| *A61Q 17/04* | (2006.01) |

(52) U.S. Cl.
USPC ............................ 424/59; 424/400; 424/401

(58) Field of Classification Search
USPC .......................................................... 424/59
See application file for complete search history.

(56) References Cited

U.S. PATENT DOCUMENTS

| 4,321,919 A | 3/1982 | Edelson |
| 4,387,089 A | 6/1983 | DePolo |
| 4,994,263 A | 2/1991 | Lang et al. |
| 5,399,719 A | 3/1995 | Wollowitz et al. |
| 5,405,868 A | 4/1995 | Goupil |
| 5,962,512 A | 10/1999 | Goupil et al. |
| 6,420,570 B1 | 7/2002 | Wollowitz et al. |
| 6,469,052 B2 | 10/2002 | Wollowitz et al. |
| 6,552,286 B2 | 4/2003 | Yang et al. |

FOREIGN PATENT DOCUMENTS

| CA | 1097224 | 3/1981 |
| JP | 6069014 | 4/1985 |
| JP | 8133964 | 5/1996 |

OTHER PUBLICATIONS

Kawada, A. et al., "An Evaluation of Broad-Spectrum Sunscreens Against Topical Puva-Induced Erythema", ACTA Dermato-Venereologica, vol. 69, No. 4, 1989, pp. 335-337.
Takeuchi, T. et al., "A Novel in Vivo Model for Evaluating Agents that Protect Against Ultraviolet A-Induced Photoaging", Journal of Investigative Dermatology, New York, New York, US, vol. 110, Apr. 1998, pp. 343-347.
Walter, J.F. et al., "Psoralen-Containing Sunscreen Induces Phototoxicity and Epidermal Ornithine Decarboxylase Activity", Journal of the American Academy of Dermatology 1982 United States, vol. 6, No. 6, 1982, pp. 1022-1027.
Rippke, F. et al., "PUVA Therapy of Psoriases—Test Model and Field of Application for UVA Protective Medicinal Sunscreens", H+G Zeitschrift Fur Hautkrankheiten 1994 Germany, vol. 69, No. 10, 1994, pp. 671-676.
Cripps, D.J. et. al., 1982. Action spectra of topical psoralens: a re-evaluation, British Journal of Dermatology 107, 77-82.
Edelson, R. et. al., 1987. Treatment of Cutaneous T-Cell Lymphoma by Extracorporeal Photochemotherapy, New England Journal of Medicine, 316:297.
Edelson, R. et. al., 1988. Light-activated Drugs, Scientific American. p. 68-75.
Fahmy, I.R. et al, 1948. Ammi Majus Linn: Pharmacognostical Study and Isolation of Crysallie Constituent, ammoidin. Quant. J. Pharmac. and Pharmacol. 20:281.
Frederiksson, T. et al, 1978. Severe Psoriasis—Oral Therapy with a New Retinoid, Dermatologica 157:238-244.
Gilchrest, B.A., et al., 1976. Oral Methoxsalen Photochemotherapy of Mycosis fungoides, Cancer 38:683-689.
Honigsmann, Herbert et al., 1984. Photochemotherapy for cutaneous T cell lymphoma. J. American Academy of Dermatology 10:238-245.
Rhodes, L.E. et al., 2000. Guidelines for topical PUVA: a report of a workshop of the British Photodermatology Group. 142:22-31.
Martens-Lobenhoffer, J. et al., 1999. Long-term Stability of 8-Methoxypsoralen in Oinitments for topical PUVA therapy (Cream-PUVA). 12:266-270.

*Primary Examiner* — Mina Haghighatian
*Assistant Examiner* — Luke Karpinski
(74) *Attorney, Agent, or Firm* — Verrill Dana, LLP; Chris A. Caseiro

(57) ABSTRACT

Compositions containing a photoactivable agent and an agent that absorbs or blocks extraneous radiation during phototherapy are useful and used in methods to treat leukocyte mediated autoimmune diseases such as psoriasis, CTCL, and vertiligo.

10 Claims, No Drawings

PHOTOTHERAPY COMPOSITIONS AND METHODS

CROSS REFERENCE TO RELATED APPLICATIONS

This application is a divisional of, and claims priority to, U.S. Non-Provisional Application Ser. No. 11/311,714, filed Dec. 19, 2005, now U.S. Pat. No. 8,057,785; which claims priority to U.S. Provisional Application Ser. No. 60/638,213, filed Dec. 22, 2004, the contents of each application are relied upon and incorporated herein by reference.

BACKGROUND OF THE INVENTION

This invention relates to topical compositions of photoactivable agents and agents for absorbing or blocking extraneous radiation during phototherapy. The compositions are useful in methods for the treatment of various disorders such as psoriasis, CTCL, vertiligo, and other leukocyte mediated diseases.

A number of human diseases are mediated by certain types of leukocytes such as lymphocytes. Excessive or abnormal lymphocyte populations can result in numerous adverse effects to patients including the functional impairment of bodily organs, leukocyte mediated autoimmune diseases and leukemia related disorders. Some of these abnormal leukocyte mediated conditions can be alleviated effective using phototherapy in conjunction -with psoralens. (See New England Journal of Medicine. 316:297 (1987); and Scientific American, August 1988, p. 68). The combination of psoralen ingestion or application together with UVA light to the skin is referred to as PUVA therapy. The psoralen is acts as a photosensitizer for the UVA treatment of the effected skin.

PUVA treatments involving the oral administration of 8-MOP followed by exposure to ultraviolet-A (UVA light 320-400 nm wavelength) is often efficacious in the management of debilitating psoriasis vulgaris, a hyperproliferative disease of the epidermis. It has also been demonstrated that plaque stage cutaneous T cell lymphoma (CTCL), when limited to the skin, can respond favorably to this treatment (Gilchrest B. A., et al. Cancer (1976) 38: 683-689; Honigsmann H., et al. J. Am. Acad. Derm. (1984) 10:238-245).

There are several disadvantages with oral PUVA. In oral PUVA therapy, patients can experience nausea or find it difficult to achieve therapeutic levels of the psoralen. Additionally patients who can be treated with current oral dosages of methoxsalen may suffer from phototoxicity if they do not avoid sunlight or artificial sources of UVA light for 24 hours after receiving therapy. Other disadvantages include exposure of the affected skin area and the area surrounding the affected area with incidental UVB and or UVA radiation.

To avoid the systemic side effects of oral PUVA, topical PUVA treatments have been used in some cases. Psoralens such as 8 MOP tend to rapidly diffuse into and out of the skin making application to skin and treatment time thereafter difficult to manage. One approach to such PUVA treatment is the so-called "Bath PUVA" treatment in which the psoralen is essentially washed onto the patient in widespread fashion followed by broad UVA exposure. Bath PUVA has been used to treat dermatoses such as in lichen planus, systemic sclerosis and generalized morphoea, urticaria pigmentosa, mycosis fungoides, polymorphic light eruption, prurigo simplex subacuta, nodular prurigo, aquagenic pruritus, and lymphomatoid papulosis. See See Rhodes L. E. *Guidelines for topical PUVA: a report of a workshop of the British Photodermatology Group*, British Journal of Dermatology, 2000: 142: 22-31.

Other more locally applied topical psoralen formulations such as ointment, paint, aqueous gel, emulsion, lotion, and/or cream have also been used to treat dermatoses. These dermatoes include atopic dermatitis, lichen planus, systemic slerosis and generalized morphoea, vitiligo, uraemic pruitus, hyperkeratotic eczema, dyshidrotic eczema, hyperkeratotic psoriasis, and palmoplantar pustulosis. See Rhodes L. E. *Guidelines for topical PUVA: a report of a workshop of the British Photodermatology Group*, British Journal of Dermatology, 2000: 142: 22-31.

While topical PUVA treatments avoid the gastrointestinal and other systemic side-effects, topical PUVA treatments, as with oral and bath PUVA treatments, still suffer from the incidental exposure to UV radiation in the affected skin area and the surrounding skin area. For a PUVA treatment, commercially available high output UVA (320-400 nm) tube-style are utilized. However, these UVA radiation sources also emit some radiation in the 290-320 nm UVB region. Thus patients undergoing PUVA treatment are also exposed inadvertently to UVB radiation. Side effects include erythema, blistering and hyperpigmentation of the surrounding skin.

Psoralen formulations and method of treatments which allow a patient to undergo efficacioius PUVA treatments while minimizing exposure to incidental radiation in the affected area as well as in the area surrounding the affected area would be welcomed.

Current 8-MOP formulations, such as paints or ointments do not protect patients from UVB exposure and do not provide a means for protecting the area surrounding the affected area.

Despite the developments in psoralen compositions and methods of using them there remains a need for a psoralen formulation that is effective for phototherapy with UVA while protecting the affected area from residual UVB emitted by the irradiation source. The psoralen-based formulations provided in this specification comprise a UVB absorbing agent for providing such protection to the affected areas of the skin. The methods of the instant invention also alleviate undesirable incidental UVB and UVA radiation by administering to the area surrounding the affected area with a composition containing UVB and/or UVA absorbing agents.

The compositions of this invention comprise an oil phase having non-volatile compounds, photoactivable compounds such as a psoralen, and an UVB absorber. The oleaginous compositions of this invention contain a psoralen and an UVB absorbing agent in an essentially non-aqueous formulation.

The present invention also includes an improved PUVA method for treatment of diseases such as atopic dermatitis, lichen planus, systemic slerosis and generalized morphoea, vitiligo, uraemic pruitus, hyperkeratotic eczema, dyshidrotic eczema, hyperkeratotic psoriasis, and palmoplantar pustulosis. The affected skin areas are treated with UVA light and a pharmaceutically acceptable composition containing a psoralen and block out inadvertent UV radiation in the area surrounding the affected area with UVA and UVB absorbing agents.

SUMMARY OF THE INVENTION

In one aspect of the invention a composition useful for PUVA therapy comprises a photoactivable substance and an agent that blocks or absorbs extraneous radiation. It can be in the form of an oil-in-water emulsion effective to alleviate at least one symptom of psoriasis, vitiligo, cutaneous T-cell lymphoma, sleroma, chronic lymphocytic leukemia, atopic dermatitis, or adult T-cell leukemia. The agent that blocks or absorbs extraneous radiation can be a UVB absorber.

In another aspect of the invention, the composition is in the form of an oil, ointment, cream, lotion, gel, or paste effective to alleviate at least one symptom of psoriasis, vitiligo, cutaneous T-cell lymphoma, sleroma, chronic lymphocytic leukemia, atopic dermatitis, or adult T-cell leukemia, in which the photoactivable compound is a psoralen selected from 5-methoxypsoralem; 8-methoxy-psoralen; 4,5'8-trimethylpsoralen; 4-methylpsoralen; 4,4-dimethylpsoralen; 4-5'-dimethyl-psoralen; 4'-aminomethyl-4,5',8-trimethyl-psoralen; 4'-hydroxymethyl-4,5',8-trimethylpsoralen; and 4',8-methoxy psoralen; and the UVB absorbing agent is selected from 3-(4-methylbenzylidene)camphor; 3-benzylidenecamphor; 2-ethyl-hexyl 4-(dimethylamino)benzoate; amyl 4-(dimethylamino)-benzoate, ethyl 4-(dimethylamino)benzoate, n-butyl 4-(dimethylamino)benzoate, i-propyl 4-(dimethylamino)-benzoate, i-amyl 4-(dimethylamino)benzoate, n-amyl 4-(dimethylamino)benzoate, cyclohexyl 4-(dimethylamino)-benzoate, n-octoyl 4-(dimethylamino)benzoate ; 2-ethyl-hexyl 4-methoxycinnamate; isopentyl 4-methoxycinnamate; i-propyl 4-methoxycinnamate, i-amyl 4-methoxycinnamate, cyclohexyl 4-methoxycinnamate; 2-ethylhexyl salicylate, 4-isopropylbenzyl salicylate; 3,3,5-trimethyl-cyclohexyl salicylate; 2-hydroxy-4-methoxybenzophenone; 2-hydroxy-4-methoxy-4'-methyl-benzo-phenone; 2,2'-dihydroxy-4-methoxy-benzophenone; and di(2-ethylhexyl) 4-methoxybenzalmalonate.

The composition can have a photoactivable compound concentration of about 0.01-10% by weight of said composition.

The composition can have a concentration of agent that blocks or absorbs extraneous radiation (preferably, UVB absorbing agent) about 0.05-2% by weight of said composition.

In yet another aspect of the invention, a method to alleviate at least one symptom of psoriasis, vitiligo, cutaneous T-cell lymphoma, sleroma, chronic lymphocytic leukemia, atopic dermatitis, or adult T-cell leukemia comprises the steps of a) contacting a composition containing a photoactivable compound and an agent that blocks or absorbs extraneous radiation to an affected area, b) contacting an area surrounding the affected area with agent that blocks or absorbs extraneous radiation (preferably, a UVB and/or UVA absorbing agent); and c) irradiating the affected area with UVA.

In yet a further aspect of the invention, a PUVA method involves the use of a photoactivable compound that is a psoralen selected from 5-methoxypsoralen; 8-methoxpsoralen; 4,5'8-trimethylpsoralen; 4-methylpsoralen; 4,4-dimethylpsoralen; 4-5'-dimethyl-psoralen; 4'-aminomethyl-4,5',8-trimethylpsoralen; 4'-hydroxymethyl-4,5',8-trimethylpsoralen; and 4',8-methoxy psoralen or combinations thereof; and the UVB absorbing agent is selected from 3-(4-methylbenzylidene)camphor; 3-benzylidenecamphor; 2-ethyl-hexyl 4-(dimethylamino)benzoate; amyl 4-(dimethylamino)-benzoate, ethyl 4-(dimethylamino)benzoate, n-butyl 4-(dimethylamino)benzoate, i-propyl 4-(dimethylamino)-benzoate, i-amyl 4-(dimethylamino)benzoate, n-amyl 4-(dimethylamino)benzoate, cyclohexyl 4-(dimethylamino)-benzoate, n-octoyl 4-(dimethylamino)benzoate ; 2-ethyl-hexyl 4-methoxycinnamate; isopentyl 4-methoxycinnamate; i-propyl 4-methoxycinnamate, i-amyl 4-methoxycinnamate, cyclohexyl 4-methoxycinnamate; 2-ethylhexyl salicylate, 4-isopropylbenzyl salicylate; 3,3,5-trimethyl-cyclohexyl salicylate; 2-hydroxy-4-methoxybenzophenone; 2-hydroxy-4-methoxy-4'-methyl-benzo-phenone; 2,2'-dihydroxy-4-methoxy-benzophenone; and di(2-ethylhexyl) 4-methoxybenzalmalonate or combinations thereof.

In another aspect of the invention, a method to alleviate at least one symptom of psoriasis, vitiligo, cutaneous T-cell lymphoma, sleroma, chronic lymphocytic leukemia, atopic dermatitis, or adult T-cell leukemia comprises the steps of a) contacting a therapeutic composition having 8-MOP and octyl methoxycinnamate, b) contacting a composition having octyl methoxycinnate to an area surrounding the affected area, and c) irradiating the area with UVA.

DETAILED DESCRIPTION

The formulations of the invention are most conveniently prepared in a form such as a gel, lotion, or ointment. The formulations contain an agent that prevents the absorption (by the patient's skin) of unwanted energy or radiation during the course of therapy. The agent can either block or absorb the unwanted or extraneous radiation. Preferably, this agent is an energy absorbing agent and most preferably it is a UVB absorbing agent. The formulation also contains an adequate amount of a photoactivable compound, preferably a psoralen, that can be applied topically to a patient's skin lesions and, when allowed to adsorb into the skin for a specified period of time, and exposed with appropriate radiation, provides an effective treatment for the disorders that can be effected by PUVA treatment. Radiation can be applied in a standard UVA PUVA light box or with a more tailored application of such radiation. After the appropriate dose of light is applied the patient would remove the topical formulation by showering, washing the affected area, or using a wipe or removal solvent.

Application of the formulation topically resolves the poor bioavailability issue and eliminates the nausea experienced by patients utilizing the oral formulation. Likewise, photoxicity can be greatly reduced. Furthermore, the topical formulation of the present invention absorbs radiation that is not of therapeutic value according to the treatment. This extraneous radiation is ordinarily in the UVB range.

Photoactivatable compounds for use in accordance with the present invention preferably include compounds known as psoralens (or furocoumarins) as well as psoralen derivatives such as those described in, for example, U.S. Pat. Nos. 4,321,919 and 5,399,719. The photoactivable compounds that can be used in accordance with the present invention include psoralen and psoralen derivatives; 8-methoxypsoralen; 4,5'8-trimethylpsoralen; 5-methoxypsoralen; 4-methylpsoralen; 4,4-dimethylpsoralen; 4-5'-dimethylpsoralen; 4'-aminomethyl-4,5',8-trimethylpsoralen; 4'-hydroxymethyl-4,5',8-trimethylpsoralen; 4',8-methoxypsoralen; and a 4'-(omega-amino-2-oxa) alkyl-4,5',8-trimethylpsoralen, including but not limited to 4'-(4-amino-2-oxa)butyl-4,5',8-trimethylpsoralen. In one embodiment, the photosensitive compound comprises the psoralen derivative amatosalen S-59, (2)3-[(2-Aminoethoxy)-methyl]-2,5,9-trimethyl-7H-furo[3,2-g][1]benzo-pyran-7-onehydrochloride (Cerus, Corp., Concord, Calif.). See, e.g., U.S. Pat. Nos. 6,552,286; 6,469,052; and 6,420,570 each of which is incorporated in its entirety by reference. In the most preferred embodiment, the photosensitive compound is 8-methoxypsoralen (9-methoxy-7H-furo[3,2-g][1]-benzopyran-7-one or 8-MOP). 8-Methoxysalen is a naturally occurring photoactive substance found in the seed of the Ammi majus (umbelliferae plant). See, for example, Fahmy et al., "Ammi Majus Linn. Pharmacognostical Study and Isolation of Crystalline Constituent, Ammoidia", Quant. J. Pharm. and Pharmacol., 20:281, (1948). It has the following structure:

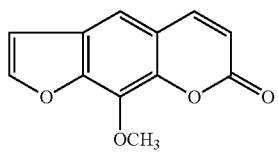

8-MOP

The agent that prevents the absorption of unwanted radiation by the patients is most preferably an energy absorbing agent. That is, the substance absorbs the radiation having the unwanted wavelengths so that it is not absorbed by the patient's skin. These substances are most preferably UVB absorbing agents and can be any compound or combination of compounds capable of absorbing ultraviolet light in the range of 290 to 320 nanometers and which are safe for use on human skin. A wide variety of UVB absorbing agents are suitable for such use. They include salts or acid neutralized forms of acidic UVB absorbing agents. Examples of such ultraviolet light-absorbing compounds include 3-benzylidenecamphor derivatives; 4-aminobenzoic acid derivatives; esters of cinnamic acid; esters of salicylic acid; derivatives of benzophenone; and esters of benzalmalonic acid. Preferred UVB absorbing agents are selected from 2-ethylhexyl-2-cyano-3,3-diphenylacrylate (referred to as octocrylene), 2-phenyl-benzimidazole-5-sulphonic acid (PBSA), cinnamates derivatives such as 2-ethylhexyl-p-methoxycinnamate and octyl-p-methoxycinnamate, TEA salicylate, octyldimethyl PABA, and mixtures thereof. Even more preferred UVB absorbing agents include 3-(4-methylbenzylidene)camphor and 3-benzylidenecamphor; 2-ethyl-hexyl 4-(dimethylamino)benzoate, amyl 4-(dimethylamino)benzoate, ethyl 4-(dimethylamino)benzoate, n-butyl 4-(dimethylamino)benzoate, i-propyl 4-(dimethylamino)benzoate, i-amyl 4-(dimethylamino)benzoate, n-amyl 4-(dimethylamino)benzoate, cyclohexyl 4-(dimethylamino)benzoate, n-octoyl 4-(dimethylamino)benzoate; 2-ethylhexyl 4-methoxycinnamate and isopentyl 4-methoxycinnamate; i-propyl 4-methoxycinnamate, i-amyl 4-methoxycinnamate, cyclohexyl 4-methoxycinnamate; 2-ethylhexyl salicylate, 4-isopropylbenzyl salicylate and homomenthyl salicylate; 2-hydroxy-4-methoxybenzophenone, 2-hydroxy-4-methoxy-4'-methylbenzo-phenone and 2,2'-dihydroxy-4-methoxybenzophenone; and di(2-ethylhexyl) 4-methoxybenzalmalonate; 2-ethylhexyl-2-cyano-3,3-diphenylacrylate (referred to as octocrylene).

The compositions preferably comprise an amount of absorbing or blocking agent that is safe and effective to provide UVB protection either independently, or in combination with, other UV absorbing agent present in the compositions. The compositions preferably comprise from about 0.1% to abut 16%, more preferably from about 0.1% to about 12%, and most preferably from about 0.5% to about 8% by weight, of absorbing or blocking agent.

The preferred compositions contain at least one UVB absorbing compound according to the present invention and at least one psoralen compound according to the present invention as well as other components used to present the combination as a topical formulation. Preferably, these other components include an oil phase component, an aqueous phase component, and/or a surfactant component for emulsifying, dispersing or solubilizing the component materials.

The compositions of this invention can also be formulated and packaged as sterile ointments and lotions in containers suitable for administering a unit dose of the composition to a subject receiving the PUVA treatment. Containers suitable for administering unit doses of formulation include syringes, ampoules, vials, tubes (e.g., those which release products when squeezed or which otherwise extrude products). The appropriate amount of the psoralen composition is added to syringe, ampoule, vial, or tube which is then stoppered or sealed and sterilized. When stoppered, a teflonized stopper is preferred.

For topical applications, lotions, ointments, or emulsions (preferably, oil-in-water emulsions) may be prepared and employed. These may be formulated with any one of a number of pharmaceutically acceptable carriers known in the art. A pharmaceutically acceptable carrier does not cause an allergic reaction or other untoward effect in patients to whom it is administered. Typical pharmaceutically acceptable carriers include, for example, one or more of water, saline, phosphate buffered saline, dextrose, glycerol, ethanol. Pharmaceutically acceptable carriers may further comprise auxiliary substances such as wetting or emulsifying agents, preservatives or buffers, which enhance the shelf life or effectiveness of the topical composition.

Preferred oil-in-water emulsions are prepared in two phases, an oil phase and an aqueous phase. In the acqueous phase, water (preferably deionized) preferably comprises at least 50 wt. % of the composition, e.g., about 50-75 wt. %.

The aqueous phase can further comprise humectant. Humectants are agents which promote the retention of moisture, e.g. moisturizers. Examples of humectants are polyhydric alcohols including polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Preferably the humectant is sorbitol. When present, amounts of humectant may range anywhere from 1 to 50%, preferably from 1 to 10%, optimally from 2 to 5% by weight.

The aqueous phase can further comprise preservatives. Preservatives are used to protect the composition form degradation. Suitable preservatives are alkyl esters of para-hydroxybenzoic acid. Other preservatives that have more recently come into use include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium Chloride, and methylbenzethonium chloride. Particularly preferred preservatives are disodium EDTA, phenoxyethanol, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the oil-in-water emulsion. Preservatives preferably are employed in amounts ranging from about 0% to about 5%, more preferably from about 0.01% to about 2.5%, and most preferably from about 0.01% to about 1%, by weight of the composition.

The aqueous phase may further comprise a water-soluble antioxidant. Antioxidants are used to protect ingredients of the composition from oxidizing agents that are included within or come in contact with the composition. The water-soluble antioxidants which are useful in the compositions of this invention include ascorbic acid, sodium metabisulfite, sodium bisulfate, sodium thiosulfite, sodium formaldehyde sulfoxylate, isoascorbic acid, thioglyerol, thiosorbitol, thiourea, thioglycolic acid, cysteine hydrochloride, 1,4-diazobicyclo-(2,2,2)-octane, malic acid, fumaric acid, licopene and mixtures thereof as well as any other known water-soluble antioxidant compatible with the other components of the compositions.

Additionally, the aqueous phase can further comprise hydrophilic gelling agents or thickeners such as the acrylic acid/ethyl acrylate copolymers and the carboxyvinyl polymers sold by the B.F. Goodrich Company under the trademark of Carbopol Registered ™ resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples of thickeners include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Thickeners such as Carbopol 934 or 940 preferably are employed in amounts ranging from 0.1% to 0.5% by weight of the composition. A higher percentage of thickeners Carbopol 934 or 940 is not desirable as psoralen 8-MOP may not be stable in a Carbopol gel. Martens-Lobenhoffer J, Rinke M, Losche D, Gollnick H; Long-Term Stability of 8-Methoxypsoralen in Ointments for Topical PUVA Therapy ('Cream-PUVA'). Skin Pharmacol Appl Skin Physiol 1999;12:266-270.

When the compositions of the invention are prepared as oil-in-water emulsions, the oil phase of the instant invention preferably contains at least one emollient oil, at least one substantive oil or wax, and at least one UVB absorbing agent. Emollient oil is an agent that softens and smoothes the skin. Emollient oil can also function as a carrier in the absorbing into the skin the photoactive agent and agent that blocks or absorbs extraneous radiation. A substantive oil also acts as a carrier. Amounts of substantive and emollient oils preferably range from about 5% to 50%, more preferably from about 20% to about 40%, and most preferably from about 30% to 40% by weight (based on total weight of the composition). Variations within this range may depend on the specific characteristics of the whole panoply of components including, for example, UVB absorbing agent, humectant, emulsifer, and gelling agent. Substantive oils and emollient oils are preferably selected from non-volatile organic oils.

Suitable substantive oil and emollient oil are preferably selected from fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof Non-volatile solvents that can be useful in the present invention may either saturated or unsaturated, have an aliphatic character and be straight or branched chained or contain alicyclic or aromatic rings. More preferably, the relatively polar, non-volatile liquid solvent are selected from the group consisting of fatty alcohols having from about 10-30 carbon atoms; fatty acids having from about 10-30 carbon atoms, for example pelargonic, lauric, myristic, palmitic, stearic, isostearic, hydroxystearic, oleic, linoleic, ricinoleic, arachidic, behenic and erucic acids and alcohols ; esters of monobasic carboxylic acids and alcohols having from about 10-30 carbon atoms; esters of dibasic carboxylic acids and alcohols having from about 10-30 carbon atoms; esters of polyhydric alcohols and carboxylic acids having from about 5-26 carbon atoms; ethoxylated, propoxylated, and mixtures of ethoxylated and propoxylated ethers of fatty alcohols with from about 12-26 carbon atoms; and mixtures thereof Suitable non-volatile organic ester oils that can be also useful in the compositions are preferably selected from one or more of the following: triglyceride esters such as vegetable and animal fats and oils; acetoglyceride esters such as acetylated monoglycerides; ethoxylated glycerides such as ethoxylated glyceryl monostearate; alkyl and alkenyl esters of fatty acids having 10 to 20 carbon atoms; ether-esters such as fatty acid esters of ethoxylated fatty alcohols; polyhydric alcohol esters such as ethylene glycol mono and di-fatty acid esters, diethylene glycol mono-and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; and liquid C1-C30 mono- and poly-esters of sugars and related materials such as glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof Other more preferred non-volatile organic oils are propoxylated ethers of C14-C18 fatty alcohols, esters of C2-C8 alcohols and C12-C26 carboxylic acids (e.g. ethyl myristate, isopropyl palmitate), esters of C12-C26 alcohols and benzoic acid (e.g. Finsolv TN supplied by Finetex), diesters of C2-C8 alcohols and adipic, sebacic, and phthalic acids (e.g., diisopropyl sebacate, diisopropyl adipate, di-n-butyl phthalate), polyhydric alcohol esters of C6-C26 carboxylic acids (e.g., propylene glycol dicaprate/dicaprylate, propylene glycol isostearate); and mixtures thereof Most preferred are esters of C12-C15 alcohols and benzoic acids (Finsolv TN).

Other more preferably non-volatile organic oils include octyl hydroxystearate, cetyl palmitate, octyl hydroxystearate, cetyl palmitate, octyl palmitate (Wickenol 155) and the like; and ethyl, isopropyl, and butyl esters of fatty acids having 10 to 20 carbon atoms such as hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

Preferred emulsifiers or surfactants used for preparing the oil-in-water emulsion can be nonionic, anionic or cationic. Illustrative nonionic surfactants are alkoxylated compounds based on C10-C22 fatty alcohols and acids, and sorbitan. These materials are available, for instance, from the Shell Chemical Company under the Neodol trademark, Copolymers of polyoxypropylene-polyoxyethylene, sold by the BASF Corporation under the Pluronic trademark, can also useful as can alkyl polyglycosides available from the Henkel Corporation. Anionic type emulsifiers or surfactants include fatty acid soaps, sodium lauryl sulphate, sodium lauryl ether sulphate, alkyl benzene sulphonate, mono- and di-alkyl acid phosphates and sodium fatty acyl isethionate. Amphoteric emulsifiers or surfactants include such materials as dialkylamine oxide and various types of betaines (such as cocamidopiopyl betaine). The overall concentration of the emulsifier can be from 0% to about 10% of the formulation, preferably from 0.1% to about 5% and most preferably from about 0.1% to about 2%, by weight of the composition.

Examples of preferred nonionic surfactants are polyoxyethylene fatty acid partial ester, polyoxyethylene sorbitan fatty acid partial ester, polyoxyethylene glycerol fatty acid partial ester, polyglycerol fatty acid partial ester, fatty acid alkanol amide, fatty acid alkanol amide-ethylene oxide addition product, polyoxyethylene glycerol fatty acid, monoglycerol pyroglutamate, and glycerol acylglutamate. Other examples of useful non-ionic surfactant include polyethylene glycol ether of stearyl alcohol of the formula CH3 (CH2)16 CH2 (OCH2 CH2)n OH, wherein n is 21; a polyethylene glycol ether of stearyl alcohol of the formula: CH3 (CH2)16 CH2 (OCH2 CH2)n OH, wherein n is 2 (available commercially as Brij 721 and Brij 72 from ICI Americas); Peregal fatty alcohol polyoxyethylene (Peregal A-20) ether having a formula RO(CH2CH2O)— 20H (a polyoxyethylene alkyl ethers), or mixture thereof.

Examples of preferred anionic surfactants are alkyl sulfate, polyoxyethylene alkyl sulfate, fatty acid amide ether sulfate, alkylbenzene sulfonate, alkyloxy sulfonate, sulfosuccinic acid higher alcohol ester salts, N-long-chain fatty acid acyl-N-methyl-taurine salts, fatty acid salts, N-long-chain acyl glutamate, N-long-chain acyl sarcosine salts, and monoalkyl phosphate.

The oil phase of the oil-in-water emulsions can also comprise an oil-soluble antioxidant. Preferred oil-soluble antioxidants useful in the compositions of the present invention include butylated hydroxytoluene (BHT), ascorbyl palmitate, butylated hydroxyanisole (BHA), phenyl-a-naphthylamine, hydroquinone, propyl gallate, nordihydroguaiaretic acid, rosemary extract and mixtures thereof The oil phase may also comprise retinoid compounds. Suitable retinoid compounds include Vitamin A alcohol (retinol), Vitamin A aldehyde (retinal) and Vitamin A esters (retinyl acetate and retinyl palmitate), although other retinoids may be incorporated into the emulsion compositions of this invention.

The oil-in-water emulsions can be prepared as cream or lotion formulations, as desired, by varying the relative quantities of the oil and water phases of the emulsion. The pH of the compositions are preferably in the range of from about 2 to about 6 since it appears that psoralens, particularly 8-MOP, tend to be more unstable in basic solution. Buffering agents can be used to maintain an established pH of the composition. Examples of buffering agents include calcium acetate, potassium metaphosphate, potassium phosphate monobasic, sodium citrate, and tartaric acid.

The oil-in-water formulations of the present invention are preferably prepared accoording well known mixing and blending procedures. For example, for emulsion products of the present invention, each phase of the emulsion is separately prepared with all of the components contained in their appropriate phases. The emulsion is formed by combining one phase to the other with agitation.

In an exemplary process for preparing such a formulation, water phase ingredients are weighed and combined slowly with agitation. Where a thickener is used such as Carbopol 934, it is preferably the last ingredient added and it too is combined slowly with agitation. The water phase is heated to about 80 C. The oil phase ingredients are weighed, combined, and heated to 80 C as well. The oil phase is then added to the water phase with agitation. The combined materials are then cooled at 45 C QS with water and homogenized for 1 minute before cooling to room temperature.

The most preferred oil-in-water emulsion is an 8-MOP Lotion with (Octyl methoxycinnamate) as the UVB absorber. The most preferred formulation is as follows:

|  | % |
|---|---|
| Water Phase | |
| Water (carrier) | 58.2 |
| Sorbitol (preservative) | 3 |
| Methyl paraben (preservative) | 0.2 |
| Carbopol 934 (thickener) | 0.3 |
| Oil Phase | |
| Brij 721(emulsifier) | 1 |
| Finsolv TN (solvent/emollient) | 12.4 |
| Octyl methoxycinnamate (UVB absorbing agent) | 7.5 |
| Wickenol 15 (emollient) | 15 |
| propyl paraben (preservative) | 0.3 |
| Sodium Stearate C-1 (thickener/barrier) | 2 |
| Methoxsalen (8-MOP) | 0.1 |
|  | 100% |

Another preferred lotion has the following formulation:

| Function | | % |
|---|---|---|
| Water Phase | | |
| Carrier | Water | 58.2 |
| Preservative | Sorbitol | 3 |
| Preservative | Methyl paraben | 0.2 |
| Thickener | Carbopol 934 | 0.3%0.3 |
| Oil Phase | | |
| Emulsifier | Brij 721 | 1.0 |
| Solvent/Emollient | Finsolv TN | 12.4 |
| UVB absorber | Octyl methoxycinnamate | 7.5 |
| Emollient | Wickenol 155 | 15 |
| Preservative | propyl paraben | 0.3 |
| Thickener/barrier | Sodium Stearate C-1 | 2 |
| Psoralen | Methoxsalen (8-MOP) | 0.1 |
|  |  | 100% |

In each case, for the oil phase methoxsalen is weighed out and added to the mixture of Finsolv TN and octyl methoxycinnamate. It is then heated to temperature with constant stirring until the methoxsalen is completely dissolved and held at that temperature for 5 minutes. The remainder of the oil phase components are then combined with it at the phasing temperature and cooled as described above.

A placebo oil-in-water emulsion useful in comparative testing of the compositions of the invention has the following formulation:

| Function | | % |
|---|---|---|
| Water Phase | | |
| Carrier | Water | 58.2 |
| Preservative | Sorbitol | 3 |
| Preservative | Methyl paraben | 0.2 |
| Thickener | Carbopol 934 (or equivalent) | 0.3 |
| Oil Phase | | |
| Emulsifier | Brij 721 | 1.0 |
| Solvent/Emollient | Finsolv TN | 12.5 |
| UVB absorber | Octyl methoxycinnamate | 7.5 |

| Function | | % |
|---|---|---|
| Emollient | Wickenol 155 | 15 |
| Preservative | propyl paraben | 0.3 |
| Thickener/barrier | Sodium Stearate C-1 | 2 |
| | | 100% |

An oleaginous formulation of photoactive agent and an agent that blocks or absorbs extraneous radiation can also be prepared from the emollient oils and substantive oils or wax as described above. Water (except for adventitious trace of water which may be present in the oil phase) is not a component of such a formulation. Preferably, the active ingredients include a psoralen such as 8-MOP and a UVB absorbing agent. Optionally, this oleaginous formulation may further comprise antioxidant such BHT, lower alkyl alcohols such as ethanol or propanol, or butanol, including mixtures thereof; animal and vegetable oils such as beeswax, Japan wax, whale wax, carnauba wax, candelilla wax, cacao oil, cetyl alcohol, stearyl alcohol, oleic acid, stearic acid, lanoline, olive oil, tsubaki oil, avocado oil, coconut oil, jojoba oil, cottonseed oil, castor oil, peanut oil, wheatgerm oil, oleyl alcohol, squalane; vaseline; oils and fats such as isopropyl myristate, isopropyl palmitate, oleyl oleate, isostearic acid, and octyl dodecanol.

The most preferred oleaginous lotion of this invention is an 8-MOP and UVB lotion having the following formulation:

| Wheatgerm oil | 1.0 g |
|---|---|
| Isopropyl Myristate | 24.9 g |
| Butyl-hydroxy-toluene | 0.1 g |
| Peanut oil q.s.p. | 100.0 g |
| 8-MOP | 0.1% |
| 2-ethylhexyl p-aminodimethylbenzoate | 2% |
| ethyl alcohol (ethanol) | 5% |

When prepared as an oleginous ointment, the following formulation is preferred:

| 8-MOP | 0.1% |
|---|---|
| | (0.1 g) |
| 2-ethylhexyl p-aminodimethylbenzoate | 2% |
| Sodium Lauryl sulfate | 1.00 g |
| Propylene glycol | 6.00 g |
| Stearylic alcohol | 10.00 g |
| Vaseline | 56.00 g |
| Methyl parahydroxybenzoate | 0.05 g |

The methods of the invention are used to alleviate at least one symptom of psoriasis, vitiligo, cutaneous T-cell lymphoma, sleroma, chronic lymphocytic leukemia, atopic dermatitis, or adult T-cell leukemia. The method of the present invention allows for both 1) protection of an area surrounding the affected area of a patient and 2) protection of the affected area from harmful extraneous (preferably UVB) irradiation. The method comprises a) contacting a therapeutical pharmaceutical composition according to the invention to an affected area; b) contacting an area surrounding the affected area with an agent that blocks or absorbs extraneous radiation agent; and c) irradiating the affected area with UVA light.

Preferable agents for blocking or absorbing extraneous radiation that are applied to areas surrounding the affected area are UVA and/or UVB absorbing agents.

Preferred UVA absorbing agents that can be used with step b) include dibenzoylmethane derivatives, anthranilate derivatives such as methylanthranilate and homomethyl, 1-N-acetylanthranilate, and mixtures thereof. Examples of dibenzoylmethane agents are described in U.S. Pat. No. 4,387,089 issued to Depolo. More preferred UVA absorbing agents are dibenzoylmethane agents and their derivatives, including but not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane, 2,6-dimethyl-4'-tert-butyl-4'methoxydibenzoylmethane, and mixtures thereof Preferred dibenzoyl agents include those selected from 4-(1,1-dimethylethyl)-4'-methoxydibenzoylmethane, 4-isopropyldibenzoylmethane, and mixtures thereof A more preferred UVA absorbing agent is 4-(1,1-dimethylethyl)-4'-methoxydibenzoylmethane.

The UVA absorbing agent 4-(1,1-dimethylethyl)-4'-methoxydibenzoylmethane, which is also known as butyl methoxydibenzoylmethane or Avobenzone, is commercially available under the names of Parsol™1789 from Givaudan Roure (International) S.A. (Basel, Switzerland) and Eusolex™9020 from Merck & Co., Inc (Whitehouse Station, N.J.). The UVA absorbing agent 4-isoproplydibenzoylmethane, also known as isopropyldibenzoylmethane, is commercially available from Merck under the name of Eusolex™ 8020.

The method of the present invention may further comprise contacting the affected area with topical steroids, topical anthralin cream (1%) or high dose/short duration anthralin in 1% salicylic acid in petroleum, or the topical synthetic retinoid tazarotene, retinoids, calcipotriene, or a vitamin D analogue (vitamin D3 or calcipotriol).

An efficacy assessment is preferably performed prior to beginning treatment, during the treatment, or after one or more elements of the treatment have been administered. For example, for psoriasis a subject is evaluated for the FDA-recommended efficacy endpoint for psoriasis medications and/or treatments. Examples of such endpoints include PASI 75 reduction or a physician global assessment. Objective methods employed for establishing the effect of treatment of psoriasis patients include the resolution of plaques by visual monitoring and with photography. The visual scoring is done using PASI (Psoriasis Area and Severity Index) score (see Fredericksson, A J, Peterssonn B C Dermatologies 157:238-244 (1978)). Topical administration is best accomplished when the composition of the invention is in the form of solutions, ointments, or creams.

Administration is best accomplished when only an effective amount of the active ingredient per unit area is involved. Illustratively a one percent solution, suspension, or ointment is applied on the order of one-tenth milliliter per square centimeter, in association with a suitable carrier, e.g., ethanol, or other carrier of types already mentioned. Following administration of the compound, the patient is irradiated with UVA at a dose ranging from 0.2 to 15 joules/cm$^2$. The amount and duration of irradiation will depend upon a number of factors including the type and the extent of the disease being treated, the age of the patient and other dosing factors known in the art.

In conventional phototherapies including prior PUVA methods, UVB and narrow band UVB, the initial dose (J/cm2) of light to be used is determined by the patient's skin type classification. (Type 1-6) The initial dose of light is started at a very low dose (enough to provide a slight light pink color to the normal skin) The dose of light energy is systematically increased during subsequent therapies. For example in existing PUVA therapy a treatment regimen would be as follows:

| Initial dose of light (J/cm2) | Increase in light dose every 3 days (J/cm2) |
| --- | --- |
| Type 1 skin 1 | 0.5 |
| Type 2 skin 2 | 1.0 |
| Type 3 skin 3 | 1.0 |
| Type 4 skin 4 | 1.0 |
| Type 5 skin 5 | 1.5 |
| Type 6 skin 6 | 1.5 |

See, Zanoli M, Feldman S, Clark A and Fleischer A, Phototherapy treatment protocols for psoriasis and other phototherapy responsive dermatoses 2000. Standard treatment rules are applied to decrease the dosage should the skin be red after any therapies or if a dose is missed. Because psoriasis plaques are more resistant to sun burning due to the amount of energy they adsorb the dose of light for the preferred method of the invention incorporates a low dose regimen that can start with a higher dose of light during initial therapies because the normal healthy skin will not be exposed to the drug or light. Therefore skin burning of healthy skin is not a concern. Higher dosages of light in the initial therapies will be followed by a decrease in light energy as the psoriasis plaque lesions heals and returns to normal skin quality. This process is an inverse of what is performed using the prior phototherapies because of the elimination of systemic exposure to normal skin. The use of higher doses of UVA light dosage in the presence of topical psoralen provides a faster response (normalization of skin) and the patient will enter a short maintenance phase at lower dose of light to prevent the normalized skin (healed psoriasis plaque) to prevent any burning of the new skin. It is also possible to use the compositions of the invention following the low dose to high treatment regimen.

EXAMPLES

Example 1

Preparation of Compositions

Two oil-in-water formulations containing methoxsalen (8-methoxypsoralen—UV photosensitizer) and octyl-methoxycinnamate (UVB sunscreen) were prepared. One formulation contained 0.09% methoxsalen, the second contained 0.01% methoxsalen. Both creams contained 7.5% octymethoxycinnamate.

The compositions were prepared as follows:
Water Phase
1. Tare main container. To this, add DI water.
2. Add Carbopol 934 slowly with propeller agitation, mix until uniform.
3. Add rest of water phase ingredients, and heat to 80 C, mix until uniform.
4. Hold at 80 C for phasing
Oil Phase
1. Into another beaker add oil phase ingredients and heat to 80 C, with propeller mixing.
2. Mix until uniform, and hold for phasing.

Phasing
1. When both phases are at 80 C and uniform, add oil phase into water phase.
2. Continue to mix until uniform.
3. When batch is uniform, cool to 45 C and QS with water.
4. Homogenize for 1 minute at 30psi.
5. Fill into appropriate container.

Formulation 1:

| I. CTFA Name | II. Trade Name | Function | Wt. % | Required |
| --- | --- | --- | --- | --- |
| Water Phase | | | | |
| Deionized Water | Water | Solvent | 58.20 | 1164.00 |
| Sorbitol 70% | Sorbitol 70% | humectant | 3.00 | 60.00 |
| Carbopol 934 | Carbomer | thicker | 0.30 | 6.00 |
| Methylparaben | Methylparaben | preservative | 0.20 | 4.00 |
| Oil Phase | | | | |
| C12-15 Alkyl Benzoate | Finsolv TN | Solubilizing agent | 12.40 | 248.00 |
| Octyl Methoxycinnamate | Parsol MCX | Sunscreen Active | 7.50 | 150.00 |
| Octyl Palmitate | Wickenol 155 | emolient | 15.00 | 300.00 |
| Propylparaben | Propylparaben | preservative | 0.30 | 6.00 |
| Steareth 21 | Brij 721 | emulsifier | 1.00 | 20.00 |
| Sodium Stearate C-1 | Sodium Stearate C-1 | emulsifier | 2.00 | 40.00 |
| Methoxsalen | | active | 0.10 | 2.00 |
| | | total: | 100.00 | 2000.00 |

Formulation 2:

| CTFA Name | Trade Name | Function | Wt. % | Required |
| --- | --- | --- | --- | --- |
| Water Phase | | | | |
| Deionized Water | Water | Solvent | 58.29 | 1165.80 |
| Sorbitol 70% | Sorbitol 70% | humectant | 3.00 | 60.00 |
| Carbopol 934 | Carbomer | thicker | 0.30 | 6.00 |
| Methylparaben | Methylparaben | preservative | 0.20 | 4.00 |
| Oil phase | | | | |
| C12-15 Alkyl Benzoate | Finsolv TN | Solubilizing agent | 12.40 | 248.00 |
| Octyl Methoxycinnamate | Parsol MCX | Sunscreen Active | 7.50 | 150.00 |
| Octyl Palmitate | Wickenol 155 | emolient | 15.00 | 300.00 |
| Propylparaben | Propylparaben | preservative | 0.30 | 6.00 |
| Steareth 21 | Brij 721 | emulsifier | 1.00 | 20.00 |
| Sodium Stearate C-1 | Sodium Stearate C-1 | emulsifier | 2.00 | 40.00 |
| Methoxsalen | | active | 0.01 | 2.00 |
| | | total: | 100.00 | 2000.00 |

A placebo formulation was also prepared as follows:

| CTFA Name | Trade Name | Function | Wt. % | Required |
| --- | --- | --- | --- | --- |
| Water Phase | | | | |
| Deionized Water | Water | Solvent | 58.20 | 1164.00 |
| Sorbitol 70% | Sorbitol 70% | humectant | 3.00 | 60.00 |
| Carbopol 934 | Carbomer | thicker | 0.30 | 6.00 |
| Methylparaben | Methylparaben | preservative | 0.20 | 4.00 |

-continued

| CTFA Name | Trade Name | Function | Wt. % | Required |
|---|---|---|---|---|
| Oil Phase | | | | |
| C12-15 Alkyl Benzoate | Finsolv TN | Solubilizing agent | 12.50 | 250.00 |
| Octyl Methoxycinnamate | Parsol MCX | Sunsceen Active | 7.50 | 150.00 |
| Octyl Palmitate | Wickenol 155 | emolient | 15.00 | 300.00 |
| Propylparaben | Propylparaben | preservative | 0.30 | 6.00 |
| Steareth 21 | Brij 721 | emulsifier | 1.00 | 20.00 |
| Sodium Stearate C-1 | Sodium Stearate C-1 | emulsifier | 2.00 | 40.00 |
| | | total: | 100.00 | 2000.00 |

Example 2

Skin Photosensitization

Both formulations were tested for ability to photosensitize human skin when applied topically followed by UVA exposure. The creams were applied to the skin of a healthy male, human volunteer and to which UVA was then applied.

The UVA exposure source was a 100W xenon arc solar simulator filtered with WG345 Schott filter. Without a photosensitizer, the UVA dose required for an erythema reaction is approximately 40 J/ $cm^2$. This filtration system eliminates virtually all radiation from the source (radiation below 340 nm). This is unlike the fluorescent UVA lamps used for PUVA therapy which contain both UVA2 and UVA1, as well as 2% UVB radiation. Comparisons of the efficacy of these two sources using an 8-MOP action spectrum (Cripps BJID 107: 77-82. 1982) shows that the fluorescent PUVA bulbs are 2.25× more effective than the solar simulator source used in the following experiments. Therefore, estimated equivalent exposures for PUVA phototherapy lamps are 2.25× lower than the exposure doses given below for the UVA filtered xenon solar simulator. Soak time refers to the time that the topical composition was allowed to stand on the subject's skin prior to UVA exposure.

| | "Soak" time | UVA exposures | Minimal Phototoxic Dose (observation Day) |
|---|---|---|---|
| Formulation 2 | 15 mins | 0.5, 0.7, 0.9, 1.3, 1.8 J/$cm^2$ | None observed |
| Formulation 1 | 15 mins | 0.7, 0.9, 1.3, 1.8, 2.5 J/$cm^2$ | None observed |

No erythema responses were observed over a three day period. It was concluded that the exposure doses used are insufficient to elicit a phototoxic erythema reaction. No erythema reaction is seen with the placebo formulation.

Higher doses of UVA exposure were then applied to determine whether they would elicit a phototoxic skin reaction. Formulation 2 was used:

| | "Soak" time | UVA exposures | Responses |
|---|---|---|---|
| Formulation 2 | 15 mins | 2.5, 4, 5, 6.3, 8.0 J/$cm^2$ | Mild erythema responses 6.3, and 8 J/$cm^{2-}$ 1 day after exposure-6 days (ongoing) |

Phototoxic reactions occurred with UVA doses of 6-8 J/$cm^2$ after only 15 minutes exposure time of the topical on the skin. The subject would have been protected from extraneous radiation in the form of UVB radiation had it been emitted.

Longer soak times between formulation application and exposure was then tested and MPD (Minimal Phototoxic Dose) UVA was determined Both concentrations of methoxsoralen cream were applied and allowed to dry and soak into the skin for 30 minutes before the start of UVA exposures with the Solar Simulator (UVA only).

| | "Soak" time | UVA exposures | Minimal Phototoxic Dose (observation Day) |
|---|---|---|---|
| Formulation 2 | 30 mins | 2.5, 4, 5, 6.3, 8 J/$cm^2$ | Progressive erythema responses starting with lowest dose observed 2 days after UVA exposure. Highest doses with deep erythema response 5 visible 5 days after exposure |
| Formulation 1 | 30 mins | 4.0, 5, 6.3, 8, 10 J/$cm^2$ | Mild erythema on the two highest doses observed 2 days pose exposure, still visible 5 days later |

Photosensitization to UVA radiation was achieved within exposure times at or below 30 minutes and well below the exposure time needed for a skin erythema reaction without the presence of the photosensitizing 8-MOP cream (40 J/$cm^2$). The subject would have been protected from extraneous radiation in the form of UVB radiation had it been emitted.

What is claimed is:

1. A composition for use in phototherapy comprising a photoactivable compound and an agent that absorbs or blocks inadvertent UV radiation generated during PUVA treatment wherein the compound is 8-methoxy-psoralen and wherein the composition together with pharmaceutically acceptable carriers is prepared in the form of a gel, lotion or ointment.

2. The composition of claim 1, wherein said psoralen concentration is about 0.01-10% by weight of said composition.

3. The composition of claim 2, wherein said psoralen concentration is about 0.01-5% by weight of said composition.

4. The composition of claim 2, wherein said psoralen concentration is about 0.05-1% by weight of said composition.

5. The composition of claim 1, wherein said agent that absorbs or blocks the inadvertent UV radiation is about 1-10% by weight of said composition.

6. The composition of claim 5, wherein said photoactivable agent is a psoralen at a concentration of about 0.1-1% by weight of said composition; and said agent that absorbs or blocks the inadvertent UV radiation is a UVB absorbing agent at a concentration of about 1-10% by weight of said composition.

7. A pharmaceutical oil-in-water emulsion composition comprising:
   from about 0.05% to about 0.4% of a psoralen;
   from about 4% to about 15% of an agent that absorbs or blocks inadvertent UV radiation during PUVA treatment;
   from about 0 to about 80% of water;

from about 10% to about 40% of a non-volatile organic oil;
from about 1 to about 5% of a thickener; and
from about 0.5% to about 2% of an emulsifier,
wherein the psoralen is 8-methoxy-psoralen.

8. The composition of claim 7 further comprising from about 0.1% to about 5% of propyl paraben.

9. A pharmaceutical oil-in-water emulsion composition comprising about 58% water, 3% sorbitol; 0.2% methyl paraben, 0.3% propyl paraben, 0.3% thickener 1% emulsifier, 12.4% solvent, 7.5% of a UVB absorber, 15% emollient, 2.0% sodium stearate C-1, and 0.1% 8-methoxypsoralen (8-MOP).

10. The composition of claim 9 further comprising an antioxidant.

* * * * *